United States Patent
Bachmann et al.

[11] Patent Number: 5,856,416
[45] Date of Patent: Jan. 5, 1999

[54] UNSATURATED CARBOHYDRATE DERIVATIVES POLYMERS THEREOF AND THEIR USE

[75] Inventors: Frank Bachmann, Freiburg, Germany; Dieter Lohmann, Münchenstein; Peter Chabrecek, Basel, both of Switzerland

[73] Assignee: CIBA Vision Corporation, Duluth, Ga.

[21] Appl. No.: 867,747

[22] Filed: Jun. 3, 1997

Related U.S. Application Data

[62] Division of Ser. No. 388,006, Feb. 13, 1995, Pat. No. 5,693,768.

[30] Foreign Application Priority Data

Feb. 15, 1994 [EP] European Pat. Off. ............. 94810084

[51] Int. Cl.⁶ .................................................. C08F 220/04
[52] U.S. Cl. ....................................................... 526/238.23
[58] Field of Search ........................................ 526/238.23

[56] References Cited

U.S. PATENT DOCUMENTS 5,196,458  3/1993  Nunez et al. ............................ 523/106

FOREIGN PATENT DOCUMENTS

| 331633 | 9/1989 | European Pat. Off. ........... C08F 8/00 |
| 513358 | 11/1992 | European Pat. Off. ......... C08B 37/16 |
| 530140 | 3/1993 | European Pat. Off. ....... C08F 299/00 |
| 3904246 | 8/1990 | Germany ...................... C07H 15/04 |
| 03046665 | 2/1991 | Japan . |
| 3221504 | 9/1991 | Japan . |
| 04314710 | 11/1992 | Japan . |
| 04316594 | 11/1992 | Japan . |
| 05295032 | 11/1993 | Japan . |
| WO9001488 | 2/1990 | WIPO . |
| WO9213894 | 8/1992 | WIPO ............................ C08B 31/00 |

OTHER PUBLICATIONS

Chemical Modification of Polymers Intended to Increase Blood Compatibility, C. H. Bamford, et al., Bull. Soc. Chim. Belg. vol. 99, 1990, pp. 919–930.

Klein, et al., Makromol Chem., vol. 191 (3):517–528, (1990)*.

Klein, et al., Makromol Chem., Rapid Commun. vol. 11(10):477–483,(1990)*.

Chemical Abstract, WPI/Derwent, JP870014925 870123, vol. 110, 1989.

Klein, Joachim, Synthesis and Characterization of New Poly(Vinyl Saccharide)s of the Urea Type, Makromol. Chem, Rapid Commun. 10, 629–636 (1989).

AS LATV Wood Chem, ALWO Aug. 8, 1979, No. 862567.

*Primary Examiner*—Bernard Lipman
*Assistant Examiner*—Nabil F. Sarofim
*Attorney, Agent, or Firm*—Michael U. Lee; R. Scott Meece

[57] ABSTRACT

The present invention relates to polymerizable derivatives of carbohydrates comprising a compound of formula (I)

$$R^1-(COO-Alk)_m-(OCONH-R)_n-(NHCO)_p-Y-Z \qquad (I)$$

wherein $R^1$ is a radically polymerizable hydrocarbon group;

m, n and p are 0 or 1;

Alk is alkylene having up to 10 carbon atoms;

R is a diradical, having up to 20 carbon atoms, of an organic diisocyanate;

Z is a monovalent radical, minus a single hydroxy group, of a mono-, di- or tri-saccharide, of an oligosaccharide, of a cyclodextrin (CD) or of an anhydrosaccharide; and Y is —O— or —NH—;

with the proviso that when p is zero, m and n are also zero and Y is —NH—; to homopolymers, copolymers, block copolymers, graft copolymers and polymeric networks thereof, to molded articles, for example contact lenses or biomedicinal articles, comprising the mentioned polymers, as well as to processes for the preparation of the mentioned polymers and articles.

8 Claims, No Drawings

UNSATURATED CARBOHYDRATE DERIVATIVES POLYMERS THEREOF AND THEIR USE

This is a division of application Ser. No. 08/388,006 filed on Feb. 13, 1995, now U.S. Pat. No. 5,693,768.

The present invention relates to polymerisable derivatives of carbohydrates comprising a carbohydrate radical, a spacer, where appropriate, and a radically polymerisable hydrocarbon group, to homopolymers, copolymers, block copolymers, graft copolymers and polymeric networks thereof, to capsules, fibers, films and coatings having water-binding and biocompatible properties, and to moulded articles, for example contact lenses or biomedicinal articles, comprising the mentioned polymers, as well as to processes for the preparation of the mentioned polymers and articles.

The introduction of polymerisable groups into carbohydrates, for example cyclodextrins (CD), is desirable on account of their properties, especially their high degree of hydrophilicity, their specific complex-forming behaviour and their biocompatibility. Acryl-containing, methacryl-containing and cinnamoyl-containing cyclodextrins and polymers thereof have been described, for example, by A. P. Croft et al. in Tetrahedron, Vol. 39, 1425 (1983). The polymerisable groups are bonded regiospecifically in the 2- or 3-position. They are obtained by reaction of appropriate activated esters, namely carboxylic acid nitrophenyl esters, with a cyclodextrin. The resulting nitrophenol can generally be removed completely only with great difficulty, since cyclodextrins form inclusion compounds with those organic compounds. Because nitrophenols are physiologically harmful, have a polymerisation-inhibiting action and also are very complicated to purify, polymers comprising such polymerisable cyclodextrins can be used to only a limited extent.

As a result of the wide variety of possible applications, especially in the pharmaceutical and related sectors, cyclodextrin derivatives comprising polymerisable groups have been widely studied. For example, such unsaturated cyclodextrin derivatives are described in WO 90/02141, WO 91/13100 and WO 92/09637. In those publications, polymers are also prepared from the mentioned unsaturated cyclodextrin monomers. Such polymers then contain cyclodextrin in immobilised form. The preparation of the mentioned unsaturated cyclodextrin derivatives is always carried out using protecting group techniques and, for example, subsequent treatment with (meth)acrylic acid chloride. In WO 92/09637, in a first step a CD is protected at the primary hydroxy group by, for example, the sterically demanding tert-butyldiphenylsilyl group, and then the remaining OH groups are etherified, the silyl protecting group is removed and the polymerisable group, (meth)acrylic acid chloride, is added. The result is in most cases unsatisfactory. Complicated synthesis and purification steps are generally required.

WO 91/17255 describes the enzyme-catalysed preparation of polymers from sugars and dicarboxylic acid esters via regioselective diacylation, the sugar radicals being bonded as comonomers in the polymer backbone and the typical properties being substantially lost as a result.

Chem. Letters 1990, 1733, describes the synthesis of anomeric glycosides without the use of protecting groups. Glucosyloxyethyl methacrylate is, for example, prepared from methyl α-D-glucopyranoside and 2-hydroxyethyl methacrylate (HEMA), with the addition of a catalyst (phosphomolybdic acid) and a polymerisation inhibitor (dinitrochlorobenzene). However, the reaction in this case is a glycosylation reaction.

In Bull. Soc. Chim. Belg. 99, 919 (1990), unsaturated carbohydrates are prepared by reaction of D-glucamine or D-glucosamine with 2-isocyanatoethyl methacrylate (IEM). The selectivity in this case is based on the differing reaction behaviour of IEM towards the functionalities that are present, that is to say OH groups versus $NH_2$ groups.

Surprisingly, it has now been found that completely unprotected carbohydrate derivatives can be reacted in a simple and selective reaction with unsaturated compounds, especially isocyanates, to form monosubstituted derivatives. As a result of such a reaction, new unsaturated carbohydrate derivatives which are modified at a single hydroxy group are isolated. Complex protecting group and unblocking techniques, as are necessary with the prior art, are not required. The resulting unsaturated carbohydrate derivatives can readily be converted into polymers having a high carbohydrate content. Homopolymers, copolymers, block copolymers and graft copolymers, linear, branched and crosslinked, can be obtained by radical polymerisation or photopolymerisation.

Accordingly, the present invention relates to a compound of formula (I)

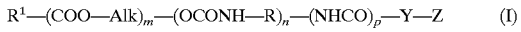

$$R^1-(COO-Alk)_m-(OCONH-R)_n-(NHCO)_p-Y-Z \quad (I)$$

wherein $R^1$ is a radically polymerisable hydrocarbon group;

m, n and p are 0 or 1;

Alk is alkylene having up to 10 carbon atoms;

R is a diradical, having up to 20 carbon atoms, of an organic diisocyanate;

Z is a monovalent radical, minus a single hydroxy group, of a mono-, di- or tri-saccharide, of an oligosaccharide, of a cyclodextrin (CD) or of an anhydrosaccharide; and Y is —O— or —NH—;

with the proviso that when p is zero, m and n are also zero and Y is —NH—.

$R^1$ is, for example, alkenyl in the form of a radically polymerisable group having preferably from 2 to 12 carbon atoms. Examples of alkenyl are vinyl, allyl, 1-propen-2-yl, 1-buten-2- or -3- or -4-yl, 2-buten-3-yl, and the isomers of pentenyl, hexenyl, octenyl, decenyl and dodecenyl. $R^1$ contains preferably from 2 to 12, more preferably from 2 to 8 and especially preferably from 2 to 4, carbon atoms.

The diradical R is, for example, lower alkylene, arylene, a saturated divalent cycloaliphatic group having from 6 to 10 carbon atoms, alkylenearylene, arylenealkylene or arylenealkylenearylene.

Arylene is preferably phenylene that is unsubstituted or substituted by lower alkyl or by lower alkoxy, especially 1,3-phenylene or 1,4-phenylene or methyl-1,4-phenylene.

A saturated divalent cycloaliphatic group is preferably cyclohexylene or cyclohexylene-lower alkylene, for example cyclohexylenemethylene, that is unsubstituted or substituted by one or more lower alkyl groups, e.g. methyl groups, for example trimethylcyclohexylenemethylene, for example the divalent isophorone radical.

Within the scope of this invention, unless defined otherwise, the term "lower" in connection with radicals and compounds denotes especially radicals or compounds having up to 7 carbon atoms, preferably up to 4 carbon atoms.

Lower alkyl has especially up to 7 carbon atoms, preferably up to 4 carbon atoms, and is, for example, methyl, ethyl, propyl, butyl or tert-butyl.

Alkylene has up to 10 carbon atoms and may be straight-chained or branched. Suitable examples include decylene, octylene, hexylene, pentylene, butylene, propylene, ethylene, methylene, 2-propylene, 2-butylene and 3-pentylene. Alkylene is preferably lower alkylene.

Lower alkylene denotes alkylene having up to 7 and especially preferably up to 4 carbon atoms. An especially preferred meaning of lower alkylene is methylene and ethylene.

The arylene component of alkylenearylene or arylenealkylene is preferably phenylene that is unsubstituted or substituted by lower alkyl or by lower alkoxy; the alkylene component thereof is preferably lower alkylene, such as methylene or ethylene, especially methylene. Accordingly, such radicals are preferably phenylenemethylene or methylenephenylene.

Lower alkoxy has especially up to 7 carbon atoms, preferably up to 4 carbon atoms, and is, for example, methoxy, ethoxy, propoxy, butoxy or tert-butoxy.

Arylenealkylenearylene is preferably phenylene-lower alkylene-phenylene having 7, and especially having up to 4, carbon atoms in the alkylene component, for example phenyleneethylenephenylene.

Within the scope of the present invention, a monosaccharide is to be understood as being an aldopentose, aldohexose, aldotetrose, ketopentose or ketohexose. The mentioned compounds may also be in the form of lactones.

Examples of an aldopentose are D-ribose, D-arabinose, D-xylose or D-lyose; examples of an aldohexose are D-allose, D-altrose, D-glucose, D-mannose, D-gulose, D-idose, D-galactose, D-talose, L-fucose or L-rhamnose; examples of a ketopentose are D-ribulose or D-xylulose; examples of a tetrose are D-erythrose or threose; and examples of a ketohexose are D-psicose, D-fructose, D-sorbose or D-tagatose.

Examples of a disaccharide are trehalose, maltose, isomaltose, cellobiose, gentiobiose, saccharose, lactose, chitobiose, N,N-diacetylchitobiose, palatinose or sucrose.

As trisaccharides there may be mentioned by way of example raffinose, panose or maltotriose.

As oligosaccharides there may be mentioned by way of example maltotetraose, maltohexaose or chitoheptaose.

Cyclodextrins contain from 6 to 8 identical units of α-1,4-glucose. Some examples are α-, β- or γ-cyclodextrin, hydroxypropylcyclodextrin or branched cyclodextrins.

An anhydrosaccharide is to be understood as being a saccharide that is formed by the removal of one or more molecules of water from a corresponding mono-, di-, tri- or oligosaccharide.

Examples of anhydrosaccharides are 1,6-anhydrosaccharides, for example levoglucosan (1,6-anhydro-β-D-glucopyranoside). Other possible variants are the isomeric 1,2-, 1,3-, 1,4- or 1,5-anhydrosaccharides. Examples of 1,4-anhydrosaccharides are anhydroerythritol or threitol.

A preferred anhydrosaccharide is, for example, levoglucosan (1,6-anhydro-β-D-glucopyranoside).

Examples of dianhydrosaccharides are 1,4:3,6-dianhydro-D-sorbitol, 1,4:3,6-anhydro-D-mannitol or 1,4:3,6-dianhydro-L-iditol.

A preferred dianhydromonosaccharide is, for example, 1,4:3,6-dianhydro-D-sorbitol.

The present invention relates also to a compound of formula (I) wherein Y is —O—.

The present invention relates also to a compound of formula (I) wherein m is 1, p is 1 and n is 0, and Y in one case is —O— and in another case is —NH—.

The present invention relates further to a compound of formula (I) wherein m and n are each zero.

The present invention relates preferably to a compound of formula (I) wherein Z is a monovalent radical, minus a primary hydroxy group, of a mono-, di- or tri-saccharide, of an oligosaccharide or of a cyclodextrin (CD).

In a preferred form of formula (I), $R^1$ is alkenyl having from 2 to 12, especially from 2 to 8 and very especially from 2 to 4, carbon atoms.

In a compound of formula (I), Alk is preferably a lower alkylene having up to 7, preferably up to 4 and more preferably up to 2, carbon atoms.

The present invention also relates preferably to a compound of formula (I) wherein the diradical R is lower alkylene, arylene, a saturated divalent cycloaliphatic group having from 6 to 10 carbon atoms, alkylenearylene, arylenealkylene or arylenealkylenearylene.

The present invention relates preferably to a compound of formula (I) wherein the radical Z is derived from a monosaccharide that is selected especially from an aldohexose and ketohexose and more especially from a 1-alkyl glucoside.

Also preferred is a compound of formula (I) wherein the radical Z is derived from a disaccharide that is selected from an α,α-, α,β- and β,β-trehalose and especially from an α,α-trehalose.

Preference is given furthermore to a compound of formula (I) wherein the radical Z is derived from a cyclodextrin that is selected from an α-, β- and γ-cyclodextrin, especially from an α- and β-cyclodextrin and more especially from an α-cyclodextrin.

Special preference is given to a compound of formula (I) wherein $R^1$ is alkenyl having from 2 to 8 carbon atoms; m and p are 1 and n is zero; Alk is a lower alkylene having up to 4 carbon atoms; Y is —O—; and the radical Z is derived from a saccharide that is a 1-alkyl glucoside, an α,α-trehalose or an α-cyclodextrin.

Special preference is given also to a compound of formula (I) wherein $R^1$ is alkenyl having from 2 to 8 carbon atoms; m, n and p are 0; Y is —NH—; and the radical Z is derived from a saccharide that is a 1-alkyl glucoside, an α,α-trehalose or an α-cyclodextrin.

Special preference is given also to a compound of formula (I) wherein $R^1$ is alkenyl having from 2 to 8 carbon atoms; m and n are zero and p is 1; and the radical Z is derived from a saccharide that is a 1-alkyl glucoside, an α,α-trehalose or an α-cyclodextrin.

Very special preference is given to a compound of formula (I) wherein $R^1$ is alkenyl having from 2 to 4 carbon atoms; m is 1, p is 1 and n is 0; and Alk is lower alkylene having up to 4 carbon atoms.

Very especially preferred is a compound of formula (I) wherein $R^1$ is alkenyl having from 2 to 4 carbon atoms; m is 1, p is 1 and n is 0; Y is —O—; and Alk is lower alkylene having up to 4 carbon atoms.

Also very especially preferred is a compound of formula (I) wherein $R^1$ is alkenyl having from 2 to 4 carbon atoms; m is 1, p is 1 and n is 0; Y is —O—; Alk is lower alkylene having up to 4 carbon atoms; and Z is a monovalent radical, minus a primary hydroxy group, of a mono-, di- or tri-saccharide, of an oligosaccharide or of a cyclodextrin (CD).

The present invention relates also to a process for the preparation of a compound of formula (I) as defined above, which process comprises reacting a saccharide of formula (II)

$$Z-X \qquad (II),$$

wherein Z is as defined above and X is a reactive group, with a derivative of formula (III)

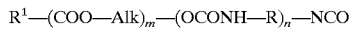
(III)

or with a derivative of formula (IV)

(IV), wherein the variables are as defined above.

The reactive group X is typically a hydroxy group or an amino group, which yields a urethane or a urea with an isocyanate of formula (III).

When ZX is reacted with a compound of formula (IV), X is generally a nucleofugal (leaving) group and is especially esterified or etherified hydroxy.

Examples of esterified hydroxy are 4-toluenesulfonyloxy, 4-bromosulfonyloxy, methanesulfonyloxy and trifluoromethylsulfonyloxy, a halide, such as a chloride, bromide or iodide, and arylcarbonyloxy, such as dinitrobenzoyloxy or benzoyloxy.

The compounds according to the invention can be prepared in the presence or absence of a solvent. Advantageously, a solvent is used that is substantially inert, that is to say that does not take part in the reaction. Suitable examples of such solvents are ethers, such as tetrahydrofuran (THF), diethyl ether, diethylene glycol monomethyl ether or dioxane, tetrahydrofuran (THF), diethyl ether, diethylene glycol monomethyl ether or dioxane, halogenated hydrocarbons, such as chloroform or methylene chloride, dipolar aprotic solvents, such as acetonitrile, acetone, dimethylformamide (DMF), hexamethylphosphoramide (HMPA), N-methylpyrrolidone (NMP) or dimethyl sulfoxide (DMSO), alcohols, such as ethanol or methanol, and also pyridine or N-methylmorpholine.

In the preparation of the compounds according to the invention, the reactants are advantageously employed in equimolar amounts. The reaction temperature may be, for example, from $-30°$ to $150°$ C. The range from $0°$ C. to room temperature is a preferred temperature range. The reaction times are in the range of approximately from 15 minutes to 7 days, preferably approximately 12 hours. If necessary, the reaction is carried out under argon or nitrogen as protecting gas.

The present invention relates also to a polymer comprising a polymerisation product of at least one compound of formula (I) according to the definition given above and optionally of at least one other vinylic comonomer (a) that is different therefrom.

The preferred composition of a polymer according to the invention is as follows: the proportion by weight, based on the total polymer, of a compound of formula (I) is in the range of from 100 to 0.5%, especially in the range of from 80 to 2% and preferably in the range of from 70 to 5%.

In a preferred polymer comprising a polymerisation product of at least one compound of formula (I), the comonomer (a) is absent and the said polymer is a homopolymer.

A comonomer (a) that is present in a polymer according to the invention may be hydrophilic or hydrophobic, or a mixture of the two. Suitable comonomers include especially those which are customarily used in the manufacture of contact lenses and biomedicinal materials.

A hydrophobic comonomer (a) is to be understood as being a monomer that, as a homopolymer, typically yields a polymer that is insoluble in water and can absorb less than 10% by weight water.

Analogously, a hydrophilic comonomer (a) is to be understood as being a monomer that, as a homopolymer, typically yields a polymer that is soluble in water or can absorb at least 10% by weight water.

Suitable hydrophobic comonomers (a) include the following, this list not being exhaustive: $C_1$–$C_{18}$alkyl and $C_3$–$C_{18}$cycloalkyl acrylates and methacrylates, $C_3$–$C_{18}$alkyl-acrylamides and -methacrylamides, acrylonitrile, methacrylonitrile, vinyl-$C_1$–$C_{18}$alkanoates, $C_2$–$C_{18}$alkenes, $C_2$–$C_{18}$haloalkenes, styrene, lower alkylstyrenes, lower alkyl vinyl ethers, $C_2$–$C_{10}$perfluoroalkyl acrylates and methacrylates or correspondingly partially fluorinated acrylates and methacrylates, $C_3$–$C_{12}$perfluoroalkyl-ethyl-thiocarbonylaminoethyl acrylates and methacrylates, acryloxy- and methacryloxy-alkylsiloxanes, N-vinylcarbazole, $C_1$–$C_{12}$alkyl esters of maleic acid, fumaric acid, itaconic acid, mesaconic acid and the like. Preference is given to, for example, acrylonitrile, $C_1$–$C_4$alkyl esters of vinylically unsaturated carboxylic acids having from 3 to 5 carbon atoms, or vinyl esters of carboxylic acids having up to 5 carbon atoms.

Examples of suitable hydrophobic comonomers (a) include methyl acrylate, ethyl acrylate, propyl acrylate, isopropyl acrylate, cyclohexyl acrylate, 2-ethylhexyl acrylate, methyl methacrylate, ethyl methacrylate, propyl methacrylate, butyl acrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyltoluene, vinyl ethyl ether, perfluorohexylethylthiocarbonylaminoethyl methacrylate, isobornyl methacrylate, trifluoroethyl methacrylate, hexafluoroisopropyl methacrylate, hexafluorobutyl methacrylate, tris-trimethylsilyloxy-silyl-propyl methacrylate, 3-methacryloxypropylpentamethyldisiloxane and bis(methacryloxypropyl)tetramethyldisiloxane.

Preferred examples of hydrophobic comonomers (a) are methyl methacrylate and acrylonitrile.

Suitable hydrophilic comonomers (a) include the following, this list not being exhaustive: hydroxy-substituted lower alkyl acrylates and methacrylates, acrylamide, methacrylamide, lower alkyl-acrylamides and -methacrylamides, ethoxylated acrylates and methacrylates, hydroxy-substituted lower alkyl-acrylamides and -methacrylamides, hydroxy-substituted lower alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2- and 4-vinylpyridine, vinylically unsaturated carboxylic acids having a total of from 3 to 5 carbon atoms, amino-lower alkyl- (the term "amino" also including quaternary ammonium), mono-lower alkylamino-lower alkyl- and di-lower alkylamino-lower alkyl-acrylates and -methacrylates, allyl alcohol and the like. Preference is given to, for example, N-vinyl-2-pyrrolidone, acrylamide, methacrylamide, hydroxy-substituted lower alkyl acrylates and methacrylates, hydroxy-substituted lower alkyl-acrylamides and -methacrylamides, and vinylically unsaturated carboxylic acids having a total of from 3 to 5 carbon atoms.

Examples of suitable hydrophilic comonomers (a) include hydroxyethyl methacrylate, hydroxyethyl acrylate, hydroxypropyl acrylate, ammonium ethyl methacrylate hydrochloride, acrylamide, methacrylamide, N,N-dimethylacrylamide, allyl alcohol, vinylpyridine, glycerol methacrylate, N-(1,1-dimethyl-3-oxobutyl)acrylamide, N-vinyl-2-pyrrolidone, acrylic acid, methacrylic acid and the like.

Preferred hydrophilic comonomers (a) are 2-hydroxyethyl methacrylate, acrylamide, N,N-dimethylacrylamide and N-vinyl-2-pyrrolidone.

The polymers according to the invention are formed in a manner known per se from the corresponding monomers by means of a polymerisation reaction known to the person skilled in the art. Customarily, a mixture of the above-mentioned monomers is heated, with the addition of a radical-former. Such a radical-former is, for example, azaisobutyronitrile (AIBN), potassium peroxodisulfate, dibenzoyl peroxide, hydrogen peroxide, sodium percarbonate etc. If, for example, the mentioned compounds are heated, then there are formed, with homolysis, radicals which may then, for example, induce polymerisation.

Especially preferred are redox polymerisation initiators, for example the mixtures ammonium peroxodisulfate/sodium disulfite or $Fe^{2+}$ (e.g. $FeSO_4$)/hydrogen peroxide.

Polymerisation may be carried out in the presence or absence of a solvent In principle, there are suitable as solvent all solvents that dissolve the monomers used, for example water, alcohols, such as lower alkanols, for example ethanol or methanol, and also carboxylic acid amides, such as dimethylformamide, dipolar aprotic solvents, such as dimethyl sulfoxide, as well as mixtures of suitable solvents, for example mixtures of water with an alcohol, for example a water/ethanol or water/methanol mixture.

The present invention relates also to polymeric networks which consist essentially of a polymer comprising a polymerisation product of at least one compound of formula (I) and optionally of at least one other vinylic comonomer (a) that is different therefrom, in crosslinked form.

The present invention relates also to polymeric networks which consist essentially of a polymer comprising a polymerisation product of at least one compound of formula (I) in the absence of a comonomer (a), in crosslinked form.

The present invention relates also to a process for the preparation of polymeric networks, which process comprises crosslinking a polymer according to the invention, for example by means of high-energy or ionising radiation, or by means of a chemical reaction, for example by reaction with a crosslinking agent, for example a diisocyanate.

The crosslinking of a polymer according to the invention is effected, where appropriate with the addition of a preferably divinylic comonomer, for example allyl (meth)acrylate, lower alkylene glycol di(meth)acrylate, divinyl ether, divinylbenzene, di(meth)acrylate of bisphenol A, methylenebis(meth)acrylamide or diallyl phthalate, by radical crosslinking or preferably by photocrosslinking.

In the case of photocrosslinking it is appropriate to add a photoinitiator which can initiate radical crosslinking. Examples thereof are known to the person skilled in the art; there may be mentioned specifically as suitable photoinitiators benzoin methyl ether, 1-hydroxycyclohexyl phenyl ketone, and Darocur and Irgacure types, especially Darocur 1173® and Irgacur 2959®. Crosslinking can then be initiated by means of actinic radiation, for example UV light of a suitable wavelength.

Also suitable are photoinitiators that are incorporated into the polymer prior to the crosslinking step. Examples of especially suitable photoinitiators are known to the person skilled in the art and are especially derivatives of Irgacure 2959® which have been esterified by, for example, methacrylic acid. A methacrylic acid esterified by, for example, Irgacur 2959® can then be incorporated into a polymer as a specific monomer. Such a polymer is then suitable for crosslinking directly, without the addition of a photoinitiator.

Crosslinking is carried out, where appropriate, in a solvent. In principle, there are suitable as solvent all solvents that dissolve the polymers, for example water, alcohols, such as lower alkanols, for example ethanol or methanol, and also carboxylic acid amides, such as dimethylformamide, or dimethyl sulfoxide, as well as mixtures of suitable solvents, for example mixtures of water with an alcohol, e.g. a water/ethanol or water/methanol mixture.

The polymers and polymeric networks according to the invention can be processed in a manner known per se to form moulded articles, especially contact lenses, for example by carrying out the photocrosslinking of the polymers according to the invention in a suitable contact lens mould. The invention therefore relates also to moulded articles that consist essentially of polymers or polymeric networks according to the invention. Further examples of moulded articles according to the invention, in addition to contact lenses, are biomedicinal articles and, especially, ophthalmic moulded articles, for example artificial corneas, intraocular lenses, eye dressings, moulded articles for use in surgery, such as heart valves, artificial arteries or the like, and also films or membranes, for example membranes for controlling diffusion, photostructurable foils for information storage, or photoresist materials, for example membranes or moulded articles for etching resist or screen printing resist.

A specific embodiment of the invention relates to contact lenses that comprise a polymeric network according to the invention or that consist essentially or completely of a polymeric network according to the invention. Such contact lenses exhibit a range of unusual and highly advantageous properties. Of those properties, mention may be made of, for example, their excellent tolerability by the human cornea and by lachrymal fluid, which is based on a balance of water content, oxygen permeability and mechanical and adsorptive properties. Moreover, the contact lenses according to the invention exhibit high dimensional stability.

All the above-mentioned advantages naturally apply not only to contact lenses but also to other moulded articles according to the invention.

The present invention relates also to a contact lens that is obtainable by crosslinking a polymer according to the invention.

A specific application of the polymers and polymeric networks according to the invention is in delivery systems for biologically active ingredients, for example pharmaceutically active ingredients (drug delivery systems). The polymers and polymeric networks according to the invention have a gel structure in which organic compounds, especially pharmaceutically active organic compounds, may be incorporated, if desired. If such polymers are administered locally, for example, then the pharmaceutically active ingredients exhibit their action firstly by slow and continuous release, that is to say in a diffusion-controlled manner, and secondly in a locally restricted manner, since they are bonded to a substrate (carrier).

The present invention relates also to the use of the monomers of formula (I) according to the invention, or of the above-mentioned polymers prepared therefrom, for coating a base material, for example glass, ceramics or metal, and preferably for coating polymer substrates, for example products for ophthalmic use, such as contact lenses, intraocular lenses or eye dressings, and products for use in medicine.

The compounds of formula (I) and the polymers prepared therefrom are especially suitable for coating preformed polymer substrates, especially products for ophthalmic use, such as contact lenses, with a hydrophilic film.

Polymer substrates are therefore to be understood as being especially substrates made from materials that are typically used for ophthalmological lenses, especially contact lenses.

Suitable polymer substrates are, for example, RGP (rigid gas permeable) lenses, e.g. Nefocon A (Ocusil), Pasifocon A (Paraperm-02), Telefocon B (SGP-II), Silafocon A (Polycon-2), Fluorsilfocon (Fluorex-400), Paflufocon A (Fluoroperm-30) or Silafocon B (Polycon-HDK); also suitable are amorphous Teflon substrates or contact lenses thereof, for example those of Teflon AF 1600 or Teflon AF 2400, the former being a copolymer of 63–73 mol % perfluoro-2,2-dimethyl-1,3-dioxole and 37–27 mol % tetrafluoroethylene, and the latter being a copolymer of 80–90 mol % perfluoro-2,2-dimethyl-1,3-dioxole and 20–10 mol % tetrafluoroethylene. Polymer substrates comprising polysiloxanes are especially suitable.

The coating of a mentioned base material is generally carried out by means of a method known to the person skilled in the art A compound of formula (I) according to the invention or a polymer prepared therefrom is bonded, for example, covalently by means of reactive groups to the surface of an article. If the material to be coated does not have any suitable reactive groups on its surface, then it is first treated, for example, with a plasma. Suitable reactive groups are thus incorporated into the surface of the said base material. Those groups can then be derivatised, for example, with a difunctional radical which is itself able to enter into a covalent bond with a compound of formula (I) according to the invention.

Examples of suitable reactive groups are hydroxy, amino, carboxy, carbonyl, sulfonyl, sulfonyl chloride and halogens, such as bromine or iodine. Preferred reactive groups are hydroxy and amino. The method of applying reactive groups such as hydroxy or amino to the surface of an article via plasma surface treatment is described comprehensively in, for example, PCT Application WO 89/00220 (Griesser et al.).

In order to be able to graft monomers of formula (D) according to the invention and the polymers prepared therefrom onto the surface of an article, the surface of the article must first be derivatised, as mentioned above. This is advantageously carried out, for example, with a difunctional radical, the functional groups of which form covalent bonds on the one hand with the hydroxy or amino groups, for example, of the surface of the article and on the other hand with the hydroxy groups, for example, of the compounds of formula (I) or the polymers prepared therefrom. The functional groups of the difunctional radical are preferably isocyanates, and the radical is selected from lower alkylene, arylene, a saturated divalent cycloaliphatic group having from 6 to 10 carbon atoms, alkylenearylene, arylenealkylene and arylenealkylenearylene.

A further method of grafting monomers of formula (I) according to the invention or polymers prepared therefrom onto the surface of an article consists essentially of bonding a photoreactive group to a monomer of formula (I) according to the invention or to a polymer prepared therefrom, which photoreactive group, when irradiated with UV light of a suitable wavelength, then couples to a surface pretreated with, for example, plasma oxygen. This method is described comprehensively in U.S. Pat. No. 5,002,582 or by R. L. W. Smithson et al., Colloids and Surfaces B: Biointerfaces, 1, 349–355 (1993).

A third method of applying monomers of formula (I) according to the invention or polymers prepared therefrom to the surface of an article comprises first bonding a reactive photoinitiator to the surface of the article and then grafting on monomers of formula (I) by means of photograft polymerisation. Specific graft polymer layers having a so-called brush structure are formed, which may also be crosslinked or branched.

The Examples given below serve to illustrate the present invention further, but they are not intended to limit the scope thereof in any way. Temperatures are given in degrees Celsius.

EXAMPLE 1

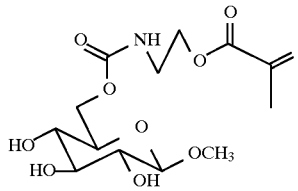

6-O-Carbamoyl-methacryloylethyl-methyl β-D-glucopyranoside 37 g (0.19 mol) of methyl β-D-glucopyranoside are dissolved at 0° C. in 500 ml of pyridine, and one molar equivalent of 2-isocyanatoethyl methacrylate (IEM) is added dropwise. The mixture is stirred for 2 days at 0° C. (TLC monitoring, eluant chloroform/MeOH 10:1). The pyridine is removed carefully by distillation at room temperature. The residue is chromatographed using chloroform/MeOH 10:1. Removal of the solvents yields 39.8 g (60%) of a colourless, hygroscopic foam.

MS(FAB): 348(M–H)$^-$, 384(M+Cl)$^-$

EXAMPLE 2

6-O-Carbamoyl-methacryloylethyl-octyl β-D-glucopyranoside

Analogously to Example 1, one molar equivalent of 2-isocyanatoethyl methacrylate is added to 208 mg (0.71 mmol) of octyl β-D-glucopyranoside. After stirring overnight, the mixture is worked up and purified analogously to Example 1, yielding 130 mg (41%) of a colourless oil.

MS(FAB): 446(M–H)$^-$, 482(M+Cl)$^-$

EXAMPLE 3

6-O-Carbamoyl-methacryloylethyl-methyl α-D-glucopyranoside 2.0 g (10.3 mmol) of methyl α-D-glucopyranoside are dissolved at 0° C. in 20 ml of pyridine. One molar equivalent of 2-isocyanatoethyl methacrylate is added to that solution. After 6 hours, a further equivalent of 2-isocyanatoethyl methacrylate is added, and the mixture is stirred overnight. After 24 hours, a third equivalent of 2-isocyanatoethyl methacrylate is added. After 36 hours, the reaction solution is diluted with 20 ml of toluene and is then concentrated. The residue is purified by chromatography over 500 g of silica gel. The eluants are: ethyl acetate (2000 ml), ethyl acetate/acetonitrile 9:1 (2000 ml), ethyl acetate/acetonitrile 1:1 (1000 ml) and methanol (1000 ml). The α-analogue of Example 1, the title compound, is obtained in the form of a colourless powder.

MS(FAB): 349(M)$^+$, 367(M+NH$_4$)$^+$

EXAMPLE 4

Methyl 6-N-(ureido-methacryloylethyl)-6-deoxy-α-D-glucopyranoside 0.276 g (1.2 mmol) of methyl 6-amino-6-deoxy-α-D-glucopyranoside hydrochloride is dissolved at 0° C. in 10 ml of pyridine, and 50 mg of diazabicyclo[2.2.2]octane are added. One molar equivalent of 2-isocyanatoethyl methacrylate is added dropwise, and the mixture is stirred overnight (TLC monitoring using ammonia [25% aqueous], ether, isopropanol 5:5:6). The reaction solution is then concentrated carefully and is purified by chromatography using the solvent mixture CH₃CN/methanol 9:1, yielding the title compound in the form of a colourless oil.

MS(FAB): 347(M−H)⁻, 383(M+Cl)⁻

EXAMPLE 5

6-O-Carbamoyl-methacryloylethyl-α,α-trehalose 40 g (0.106 mol) of α,α-trehalose are dissolved in 400 ml of pyridine, and 18.13 g (0.117 mol, 1.1 equivalents) of 2-isocyanatoethyl methacrylate are slowly added dropwise, with stirring, at room temperature. The mixture is stirred overnight. 300 ml of toluene are then added to the reaction solution, whereupon a white solid precipitates. The mixture is filtered and the residue is then washed with a small amount of toluene, yielding 39.4 g of crude product, which are dissolved in 300 ml of water. 1.2 liters of acetonitrile are slowly added to that solution, an emulsion being formed intermediately. A further liter of acetonitrile is therefore added, whereupon a white solid precipitates. The latter is filtered off and recovered as starting material (18 g, 45%). Acetone is then added to the clear solution until there is no further precipitation. The filtered solution is then concentrated. The residue that remains is dissolved in water, is washed twice with ethyl acetate, and is again concentrated, yielding the title compound in the form of a colourless solid.

$R_f$ value: 0.59 (CH₃CN/H₂O 8:2) MS(FAB): 496(M−H)⁻

| | Combustion analysis: | | |
|---|---|---|---|
| | C | H | N |
| calculated | 45.88% | 6.28% | 2.82% |
| found | 45.12% | 6.29% | 2.84% |

EXAMPLE 6

6-O-Carbamoyl-methacryloylethyl-β,β-trehalose

In a flask, under argon, 1.9 g (0.292 mmol) of β,β-trehalose are dissolved in 19 ml of dry pyridine. 861 μl (5.55 mmol) of IEM are slowly added dropwise to that solution at room temperature. A conversion can be clearly observed after only one hour. The mixture is stirred for a further 6 hours and is then worked up. 10 ml of toluene are added, whereupon a solid precipitates. The solid is dissolved in water and is purified by means of chromatography (300 g of silica gel, acetonitrile/water 9:1), yielding 1.0 g (36%) of a colourless solid.

$R_f$ value: 0.48 (CH₃CN/H₂O 8:2).

EXAMPLE 7

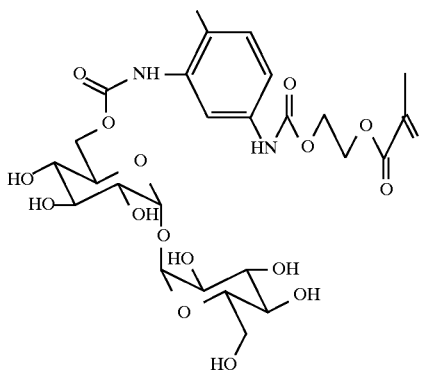

6-O-Carbamoyl-{(methacryloylethyl-O-carbamoyl)-2,4-toluoyl}-α,α-trehalose 2 g (5.3 mmol) of α,α-trehalose are dissolved at 0° C. in 100 ml of pyridine. One equivalent of 2-isocyanato-4N-(carbamoyl-methacryloylethyl)-toluene (prepared from 2,4-toluylene diisocyanate and 2-hydroxyethyl methacrylate according to U.S. Pat. No. 2,958,704) is then added. After 24 hours, the reaction mixture is concentrated under a high vacuum and the residue is purified by chromatography (silica gel, acetonitrile/water 8:2), yielding the title compound in the form of a colourless solid.

MS(FAB): 645(M−H)⁻, 669(M+Na)⁺, 681 (M+Cl)⁻

EXAMPLE 8

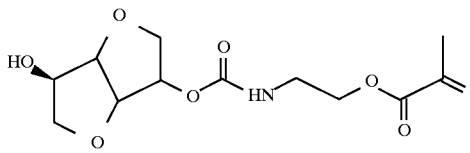

2-O- and (5-O)-monocarbamoyl-methacryloylethyl-1,4:3,6-dianhydro-D-sorbitol 5 g (34 mmol) of 1,4:3,6-dianhydro-D-sorbitol are dissolved in 50 ml of pyridine, and one equivalent of 2-isocyanatoethyl methacrylate is added at 0° C. The mixture is heated to room temperature and is then stirred overnight The reaction mixture is then concentrated and purified by chromatography (silica gel, chloroform/methanol 10:1), yielding the title compounds in the form of colourless oils.

EXAMPLE 9

6-O-Carbamoyl-methacryloylethyl-α,β-maltotriose

One equivalent of 2-isocyanatoethyl methacrylate is added at room temperature to 5 g (9.9 mmol) of maltotriose in 100 ml of pyridine. After 48 hours, 100 ml of toluene are added, and the mixture is concentrated carefully to dryness under a high vacuum. A light-yellow oil remains, which is purified by chromatography (400 g of silica gel, acetonitrile/water, first 9:1 and then 8:2), yielding 1.3 g (20%) of monoacrylate in the form of a colourless oil.

$R_f$ value: 0.35 (CH₃CN/H₂O 8:2) MS(FAB): 658(M−H)⁻, 694(M+Cl)⁻

EXAMPLE 10

6-O-Carbamoyl-methacryloylethyl-α-cyclodextrin 5 g (5.14 mmol) of α-cyclodextrin (α-CD) are dissolved in 50 ml of pyridine, and one equivalent of 2-isocyanatoethyl methacrylate is added at room temperature. After 24 hours, a suspension has formed, which is filtered. 3.9 g of α-CD starting material are thus recovered. 200 ml of toluene are then added to the clear solution, whereupon a white precipitate forms, which is filtered off with suction and is dried. The dried precipitate is dissolved in 10 ml of water, and 60 ml of acetone are added. A precipitate again forms and is filtered off and discarded. The clear solution that remains is concentrated and taken up in a small amount of methanol, and then several drops of acetonitrile are added. A white precipitate forms and is filtered off with suction and is dried, thus yielding the title compound without purification by chromatography.

Alternatively, the crude product may be prepared in pure form by purification by chromatography on silica gel using acetonitrile/water 9:1, then 8:2 and finally 7:3.

$R_f$ value: 0.24 (CH$_3$CN/H$_2$O 8:2) MS(FAB): 1126(M−H)$^−$, 1162(M+Cl)$^−$

EXAMPLE 11
6-O-Carbamoyl-methacryloylethyl-β-cyclodextrin 1.0 g (0.88 mmol) of β-CD is dissolved in 15 ml of pyridine and diluted dropwise at 0° C. with 2.74 g (1.8 mmol) of 2-isocyanatoethyl methacrylate (IEM). After 2 days, 100 ml of toluene are added to the reaction mixture, which is then concentrated completely in vacuo. The residue is chromatographed over silica gel using acetonitrile/water 8:2. Removal of the solvent yields the title compound in amorphous form.

$R_f$ value: 0.16 (CH$_3$CN/H$_2$O 8:2) MS(FAB): 1288(M−H)$^−$

EXAMPLE 12
6-O-Monoallylcarbamoyl-β-cyclodextrin 2.0 g (1.76 mmol) of β-CD are dissolved in 20 ml of pyridine, and a solution of 293 mg (3.52 mmol, 2 equivalents) of allyl isocyanate in 2 ml of pyridine is added dropwise at 0° C. After 6 hours, a further 2 equivalents of allyl isocyanate in 2 ml of pyridine are added. After 30 hours, a further 4 equivalents of allyl isocyanate are added. After 5 days, the reaction solution is diluted with 50 ml of toluene and is then concentrated completely. The residue is purified by chromatography (silica gel, acetonitrile/water 1:1). Removal of the solvent yields the compound mentioned in the title.

$R_f$ value: 0.39 (CH$_3$CN/H$_2$O 7:3) MS(FAB): 1240(M+Na)$^+$, 1348(M+Na+thioglycerol)$^+$

EXAMPLE 13
6-N-Allyl-amino-6-deoxy-β-cyclodextrin

Under argon, 100 mg (78 μmol) of 6-O-monotoluenesulfonyl-β-cyclodextrin are added in portions, with stirring, to 1.3 ml (17.5 mmol) of allylamine. The resulting suspension is heated at 70° C. for 4 hours. The reaction mixture is then concentrated to dryness by evaporation under a high vacuum. The residue is dissolved in 2 ml of water and is then precipitated by the addition of 10 ml of acetonitrile. The precipitate is filtered off with suction and is washed with a small amount of acetonitrile. Drying yields 56 mg (61%) of a colourless solid.

$R_f$ value: 0.10 (ether/NH$_3$ [25% aqueous]/isopropanol 5:6:6) MS(FAB): 1174(M+H)$^+$, 1281(M+thioglycerol)$^+$

EXAMPLE 14

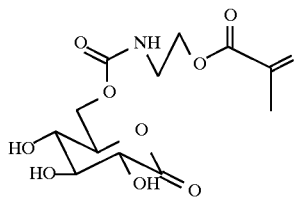

6-O-Carbamoyl-2-methylpropenoylethyl-gluconic acid γ-lactone 4.4 g (28.1 mmol) of IEM are slowly added dropwise to 5.0 g (28.1 mmol) of D(+)-gluconic acid δ-lactone in 50 ml of pyridine. The mixture is then stirred for 2 days at room temperature and is then worked up as in Example 1. Purification by chromatography (acetonitrile/water 9:1) yields 2.8 g (30%) of a colourless powder. MS(FAB): 334(M+H)$^+$, 356(M+Na)$^+$

EXAMPLE 15
6-Allylamino-6-deoxy-methyl β-D-glucopyranoside 1 ml of allylamine is added to 100 mg of 6-O-tosyl-methyl β-D-glucopyranoside, and the mixture is stirred at 40° C. for 12 hours to complete the reaction. The reaction mixture is then concentrated under a high vacuum and is subsequently purified by chromatography (acetonitrile), yielding 30 mg (42%) of a colourless oil.

EXAMPLE 16
6-O-Carbamoyl-methacryloylethyl-α,β-maltose

Analogously to Example 6, 10 g (0.027 mol) of maltose in pyridine are reacted with one equivalent of IEM. Working up and purification yield 2.9 g (22%) in the form of a colourless powder.

$R_f$ value: 0.32 (CH$_3$CN/H$_2$O 9:1) MS(FAB): 496(M−H)$^−$, 520(M+Na)$^+$, 532(M+Cl)$^−$

EXAMPLE 17
6-O-Carbamoyl-methacryloylethyl-α,β-lactose

The title compound is obtained analogously to Example 16 in a similar yield, using as starting materials lactose and IEM in pyridine.
MS(FAB): 498(M+H)$^+$, 520(M+Na)$^+$

EXAMPLE 18
2-O-Carbamoyl-methacryloylethyl-1,6-anhydro-β-glucopyranose and isomers Analogously to Example 8, 50 g (0.308 mol) of 1,6-anhydro-β-D-glucopyranoside are reacted with one equivalent of IEM in pyridine. Working up and purification yield 44 g (45%) of a monoacrylate isomeric mixture.
MS(FAB): 318(M+H)$^+$

EXAMPLE 19
6-O-Carbamoyl-methacryloylethyl-γ-cyclodextrin

Analogously to Example 11, the title compound is prepared from 20.g (15.4 mmol) of γ-CD and 7.2 g (46.3 mmol) of IEM in 250 ml of pyridine. 4.47 g (20%) of a colourless powder are obtained.

$R_f$ value: 0.36 (CH$_3$CN/H$_2$O 7:3) MS(FAB): 1475(M+Na)$^+$

EXAMPLE 20
6-O-Monoallylcarbamoyl-α-cyclodextrin

Analogously to Example 12, 20 g of α-cyclodextrin are reacted with 6.3 g (3.75 equivalents) of allyl isocyanate in pyridine. Purification yields 4 g (19%) of a colourless powder.

$R_f$ value: 0.15 (CH$_3$CN/H$_2$O 8:2) MS(FAB): 1054(M−H)$^+$

EXAMPLE 21
Synthesis of poly(6-O-carbamoyl-methacryloylethyl-methyl β-D-glucopyranoside) homopolymer A solution of 1.0 g of 6-O-carbamoyl-methacryloylethyl-methyl β-D-glucopyranoside in 4 ml of water (degassed) is cooled to 0° C. under argon. Then 50 μl of an ammonium peroxodisulfate solution (concentration of that persulfate solution is 10 mg/ml) and 50 μl of a sodium disulfite solution (concentration of that disulfite solution is also 10 mg/ml) are added. After 2 hours, the reaction solution is poured onto 400 ml of methanol, whereupon the polymer, 820 mg (82%), precipitates in the form of a fine white solid.

EXAMPLE 22
Synthesis of poly(6-O-carbamoyl-methacryloylethyl-α,α-trehalose) homopolymer In a flask, under argon, 1.0 g (2 mmol) of 6-O-carbamoyl-methacryloylethyl-α,α-trehalose is dissolved in 4 ml of degassed water (HPLC grade), and the solution is cooled to 0° C. 100 μl of an ammonium peroxodisulfate solution and 100 μl of a sodium disulfite solution (concentration as in Example 21) are added thereto. The polymerisation is monitored by TLC (acetonitrile/water 8:2). After one hour, the reaction is complete. The reaction solution is then introduced dropwise into 400 ml of methanol, whereupon a white solid precipitates. The solid is filtered off, taken up in water and lyophilised. The homopolymer is obtained in the form of a colourless amorphous powder, 900 mg (90%).

EXAMPLE 23
Synthesis of poly(6-O-carbamoyl-methacryloylethyl-β,β-trehalose) homopolymer Analogously to Example 22, 500 mg of 6-O-carbamoyl-methacryloylethyl-β,β-trehalose are polymerised in 2 ml of degassed water. Lyophilisation yields 358 mg (72%) of a white solid.

EXAMPLE 24
Synthesis of poly(6-O-carbamoyl-methacryloylethyl-α,β-maltotriose) homopolymer Analogously to Example 22, 500 mg of 6-O-carbamoyl-methacryloylethyl-α,β-maltotriose are polymerised in 2 ml of degassed water and in the presence of 50 μl of ammonium peroxodisulfate solution and 50 μl of a sodium disulfite solution. Lyophilisation yields 371 mg of a white solid.

EXAMPLE 25
Synthesis of poly(6-O-carbamoyl-methacryloylethyl-α-cyclodextrin) homopolymer 20 μl of acetonitrile are added to a suspension of 100 mg (89 μmol) of 6-O-carbamoyl-methacryloylethyl-α-cyclodextrin in 0.2 ml of water (degassed). 1 mg of ammonium peroxodisulfate and 1 mg of sodium disulfite are introduced into that solution, with stirring. The polymerisation is monitored by TLC. After 20 hours, the slightly cloudy reaction solution is poured onto 40 ml of methanol. The resulting solid is filtered off, taken up in water and lyophilised, yielding 88 mg (88%) of homopolymer.

EXAMPLE 26
Synthesis of poly(6-O-carbamoyl-methacryloylethyl-β-cyclodextrin) homopolymer In a flask, 100 mg of 6-O-carbamoyl-methacryloylethyl-β-cyclodextrin are dissolved in 0.6 ml of dry dimethylformamide (DMF). The solution is then clarified by filtration, and 10 mg of AIBN are added. The reaction mixture is degassed and is then heated to 80° C. under argon. The mixture is allowed to react at that temperature overnight. The reaction mixture is then stirred into 100 ml of methanol, whereupon a fine white solid precipitates, which is filtered off and dried.

EXAMPLE 27
Synthesis of poly-co(6-O-carbamoyl-methacryloylethyl-α,α-trehalose acrylamide) (molar ratio trehalose/acrylamide 3:1)

200 mg of 6-O-carbamoyl-methacryloylethyl-α,α-trehalose of Example 5 in degassed water are introduced into a flask, under argon. 9.5 mg (0.134 mmol) of acrylamide are added. The mixture is flushed with argon and cooled to 0° C., and then 10 μl of ammonium peroxodisulfate solution and 10 μl of sodium disulfite solution (concentration as in Example 21) are added. The reaction mixture is stirred for 3 days. 100 ml of methanol are then added, whereupon a white solid precipitates. The solid is filtered off and dried, yielding 50 mg of copolymer.

EXAMPLE 28
Synthesis of poly-co(6-O-carbamoyl-methacryloylethyl-α,α-trehalose acrylamide) (molar ratio trehalose/acrylamide 1:3)

Analogously to Example 27, 200 mg of trehalose derivative of Example 5 are copolymerised with 85.7 mg (1.2 mmol) of acrylamide. Working up as in Example 27 yields 238 mg (83%) of polymer.

EXAMPLE 29
Synthesis of poly-co(6-O-carbamoyl-methacryloylethyl-α,α-trehalose hydroxyethyl methacrylate (HEMA)) (molar ratio trehalose/HEMA 1:3)

137 mg (1.2 mmol) of HEMA (technical grade) are added to a solution of 200 mg of 6-O-carbamoyl-methacryloylethyl-α,α-trehalose of Example 5 in 0.77 ml of water, and polymerisation is carried out analogously to Example 27. After 3 hours, a water-insoluble gel is formed.

EXAMPLE 30
Synthesis of poly-co(6-O-carbamoyl-methacryloylethyl-α,α-trehalose hydroxyethyl methacrylate (HEMA)) (molar ratio trehalose/HEMA 3:1)

Analogously to Example 29, 200 mg of 6-O-carbamoyl-methacryloylethyl-α,α-trehalose and 15.3 mg (0.134 mmol) of HEMA are polymerised. No gel is formed; the reaction mixture remains a clear solution. The solution is diluted with 100 ml of methanol, whereupon a solid precipitates. The solid is filtered off, yielding 160 mg (73%).

EXAMPLE 31
Synthesis of poly-co(6-N-allyl-amino-6-deoxy-β-cyclodextrin acrylamide) (molar ratio β-CD/acrylamide 1:1)

100 mg (0.085 mmol) of 6-N-allyl-amino-6-deoxy-β-cyclodextrin of Example 13 are introduced into 2 ml of degassed water, under argon. 18 mg (0.26 mmol) of acrylamide and 26 μl of tetramethylethylenediamine are added. 26 mg of ammonium peroxodisulfate are then added in portions at 0° C. After 24 hours, the reaction solution is stirred into 40 ml of methanol. A white solid precipitates and is filtered off, taken up in water and then lyophilised, yielding 33 mg.

EXAMPLE 32
Synthesis of poly-co(6-N-allyl-amino-6-deoxy-β-cyclodextrin acrylamide) (molar ratio β-CD/acrylamide 1:3)

Analogously to Example 31, copolymerisation is carried out in the ratio 1:3. Lyophilisation yields 27 mg.

EXAMPLE 33

Synthesis of poly-co(6-O-carbamoyl-methacryloylethyl-α, α-trehalose N-vinyl-2pyrrolidone (NVP)) (molar ratio 1:1)

Analogously to Example 30, trehalose monoacrylate of Example 5 and NVP are copolymerised in water, yielding a gel.

EXAMPLE 34

Synthesis of other copolymers analogously to Example 27 shown in table form (yield in each case 75%):

| Carbohydrate derivative | Comonomer | Ratio |
|---|---|---|
| trehalose derivative of Ex. 5 | N,N-dimethylacrylamide | 3:1 |
| trehalose derivative of Ex. 5 | Nippon Blemer ® GLM | 3:1 |

EXAMPLE 35

Photopolymerisation

In a brown round-bottomed flask, 1 g of a carbohydrate monomer is dissolved in 4 ml of degassed water. An appropriate amount of any comonomer that is used and an appropriate amount of photoinitiator are added thereto. Residual air is removed by repeated evacuation and introduction of argon. The solution is then introduced into small moulds (e.g. with contact lens geometry) and is irradiated, under argon, with UV light of a suitable wavelength. The resulting moulded blanks are freed of residual monomers by extraction with water and are then examined as regards their properties.

EXAMPLE 36

Washed and dried STD™ contact lenses (CIBA Vision, Atlanta, Tefilcon) based on crosslinked poly-HEMA are soaked in a solution of 5 ml of THF, 5 ml of diethyl ether, 0.2 g of diisophorone diisocyanate (IPDI) and 10 mg of dibutyltin dilaurate (DBTDL). The lenses are left in the solution for 12 hours at room temperature and under nitrogen. The lenses are then washed with acetone, dried and then soaked in a 0.5% solution of the polymers of Examples 21, 22 and 25 in DMSO, which solution additionally contains 5% LiCl and 0.1% DBTDL as catalyst. The lenses are left in the solution for 12 hours at 25°–40° C.; they are then washed thoroughly with water and are subsequently dried. The static contact angles (CA) of the untreated and treated contact lenses are then measured using a G 40 system (Krüss GmbH, Hamburg, Germany).

| treated with polymer | static contact angle (CA) |
|---|---|
| of Example 21 | 58° |
| of Example 22 | 41° |
| of Example 25 | 32° |
| untreated lens | 78° |

EXAMPLE 37

Preparation of a Plasma-modified Polymer Surface

A silicone film, which has been prepared by UV curing of Silicon PS 2067 (Hüls America Inc., Bristol, USA), is placed in a RF-GDP (radio frequency glow discharge plasma) reactor. The reactor is evacuated to 0.1 mbar. The silicone film is then exposed for 30 seconds to an oxygen plasma at 40 watts power and an oxygen gas flow rate of 10 cm$^3$/min. (STP). The reactor is then aerated.

EXAMPLE 38

The plasma-treated film of Example 37 is placed in a desiccator over 5 ml of toluene-2,4-diisocyanate, then the desiccator is evacuated to 0.008 mbar and the mixture is heated to 50° C. The film is left in the desiccator for 2.5 hours (derivatisation with toluene-2,4-diisocyanate) and is then cooled to room temperature. The film is removed and washed with acetone. The film so pretreated is then immersed for 8 hours in a DMSO solution containing the trehalose polymer of Example 22 and 5% LiCl. The film so modified is then washed with water, dried and analysed.

EXAMPLES 39–41

Example 39

A polybutadiene film is treated with an oxygen plasma in accordance with Example 37. Subsequent exposure in toluene-2,4-diisocyanate in accordance with Example 38 is for 2.5 hours. Treatment with the trehalose polymer is for 8 hours.

Example 40

A poly-HEMA film is prepared from a solution containing HEMA (92%), ethylene glycol dimethacrylate (5%) and a photoinitiator Irgacur 184 (3%) by pouring onto a Folanorm foil and UV irradiation. Exposure in toluene-2,4-diisocyanate in accordance with Example 38 is for 6 hours. Treatment with the trehalose polymer is also for 8 hours.

Example 41

A polyvinyl alcohol (PVA) film is prepared from a DMSO solution of PVA 72 000 (Fluka) and IPDI (Aldrich) by pouring onto a Folanorm foil and heating at 70° C. for 2 hours. The film is treated further in accordance with Example 40.

The contact angles (CA) are determined as described in Example 36.

| Example | Polymer film | CA before treatment (°) | CA after treatment (°) |
|---|---|---|---|
| 38 | silicone | 100.4 | 51.6 |
| 39 | polybutadiene | 79.5 | 49.3 |
| 40 | poly-HEMA | 78.4 | 44.6 |
| 41 | PVA | 47.1 | 23.8 |

EXAMPLE 42

Preparation of

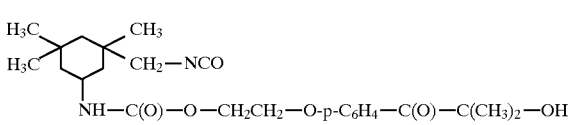

NH—C(O)—O—CH$_2$CH$_2$—O-p-C$_6$H$_4$—C(O)—C(CH$_3$)$_2$—OH

In a 500 ml flask equipped with a reflux condenser, a thermometer, a stirrer and a nitrogen inlet pipe, a solution of 11.125 g (0.05 mol) of freshly distilled isophorone diisocyanate (IPDI) in 50 ml of dry methylene chloride is mixed, under nitrogen, with a solution of 11.2 g (0.05 mol) of 4'-(β-hydroxyethoxy)-2-hydroxyprop-2-yl-phenone (Darocure 2959®) in 300 ml of dry methylene chloride; after the addition of 20 mg of dibutyltin dilaurate as catalyst, the mixture is stirred at room temperature for 48 hours. The progress of the reaction is followed by means of thin layer chromatography on silica gel plates (60 $F_{254}$, art. 5719 Merck) (eluant: toluene/acetonitrile 7:3). The resulting product is freed of small amounts of unreacted Darocure 2959 and bisadduct of IPDI by column chromatography on silica gel 60 (eluant: toluene/acetonitrile 7:3). Concentration of the pure fractions by evaporation on a rotary evaporator yields a colourless oil which crystallises slowly when cooled to −16° C. and is then recrystallised from dry diethyl ether. 15.6 g of a white crystalline product (70% of the theoretical yield) having a melting point of 76° C. are obtained.

The isocyanate content of the product is determined by titration with dibutylamine in toluene: calculated 2.242 m Val/g, found 2.25 m Val/g.

The method is described in "Analytical Chemistry of Polyurethanes" (High Polymer Series XVI/Part III, D. S. David+H. B. Staley editors, Interscience Publishers, New York 1969 p. 86).

EXAMPLE 43
Surface Reaction of a Contact Lens

Contact lenses of crosslinked polyhydroxyethyl methacrylates (poly-HEMA) are wetted on the surface with a solution of the compound of Example 42 in tetrahydrofuran (concentration 5%) or diethyl ether. The treated contact lenses are stored under dry nitrogen at room temperature for 16 hours. The contact lenses are then washed with acetone for 8 hours and are then dried under a high vacuum.

EXAMPLE 44
Modification of the Surface of a Contact Lens

Contact lenses treated in accordance with Example 43 are immersed in an aqueous solution of the monomer of Example 5 and are then freed of oxygen by repeated evacuation and relief with nitrogen. The lenses are then irradiated twice for 2 minutes, under nitrogen, using a high-pressure mercury lamp (Photoresistbelichter 82420, Oniel, 2000 W). The contact lenses are then washed with distilled water and dried under a high vacuum. Before and after treatment, the contact lenses exhibit the following values for the contact angles (advancing and receding angle) and the contact angle hysteresis. The numerical values indicate the improved hydrophilicity, the good water retention ability and the complete coating of the surface so produced.

| Contact lens | Advancing angle | Receding angle | Hysteresis (°) | Retention water film |
|---|---|---|---|---|
| poly-HEMA untreated | 78.4° | 33.3° | 45.1° | ca. 10 sec. |
| poly-HEMA treated | 41.2° | 29.9° | 11.3° | >2 min. |

EXAMPLE 45
Coating of a Polymer Substrate

A foil (2 cm×2 cm) of poly-hydroxyethyl methacrylate (poly-HEMA) and 3% diethylene glycol diacrylate (DEGDA) as crosslinking agent is introduced into a plasma reactor. The reactor chamber is then charged under glow discharge conditions with 1,2-diaminocyclohexane as plasma gas under the following conditions: radio frequency of 27.12 MHz, 3 watts power, 0.5 mbar (50 Pa) pressure, working gas flow rate 3.65 cm³/min. (STP), dwell time of the foil in the reactor is 5 minutes.

The foil so treated is then immersed for 8 hours at room temperature and under nitrogen in a THF/diethyl ether solution (1:2) containing 1% by weight of the compound of Example 42 and a catalytic amount of dibutyltin dilaurate (DBTDL). The reactive photoinitiator is thus bonded to the amino groups produced by the plasma treatment on the foil surface. The foil is then washed in THF for 3 hours and is then dried in vacuo for 3 hours. The dried foil is then introduced into a stirred 15% aqueous solution of the trehalose monomer of Example 5 and is then irradiated on both sides for 4 minutes using a high-pressure mercury lamp (2000 watts). The coated foil is then washed several times in distilled water, and the contact angles and the water retention times are then measured.

| Poly-HEMA | Advancing angle | Receding angle | Water retention time |
|---|---|---|---|
| untreated | 82.8° | 47.4° | ca. 10 sec. |
| treated | 41.2° | 29.9° | >2 min. |

EXAMPLE 46

A foil (2 cm×2 cm) of silicone rubber, prepared by crosslinking 2 mol of vinyl polysiloxane (Silopren U Additiv V 200, Bayer) with 4 mol of H-siloxane (K-3272, Goldschmidt), is treated in a plasma reactor (in accordance with Example 45) under glow discharge conditions with 1,2-diaminocyclohexane as plasma gas. The silicone film so pretreated is then immersed for 3 hours at room temperature, under nitrogen, in an acetonitrile solution containing 1% of the coreactive photoinitiator of Example 42 and 10 mg of DBTDL as catalyst. The film so treated is then washed with acetonitrile and dried in vacuo. The film is then immersed in an aqueous solution containing 1.5 g of the monomer of Example 5 in 10 ml of water. Subsequently, the film so coated is irradiated on both sides for 4 minutes using a high-pressure mercury lamp (2000 watts). The coated film is washed several times in distilled water, and the contact angles and the water retention times are then measured.

| Polymer | Advancing angle | Receding angle | Water retention time |
|---|---|---|---|
| untreated silicone | 122.4° | 101.8° | <3 sec. |
| treated silicone | 62.7° | 37.6° | >20 sec. |

EXAMPLE 47

Analogously to Example 45, a washed and dried Weicon contact lens (CIBA-Vision Atlanta) is likewise coated with the photoinitiator of Example 42 and the monomer of Example 5. The treated lens is washed several times in distilled water, and the contact angles and the water retention times are then measured.

| Weicon contact lens | Advancing angle | Receding angle | Water retention time |
|---|---|---|---|
| untreated | 78.4° | 44.3° | ca. 12 sec. |
| treated | 59.2° | 34.6° | 1.8 min. |

EXAMPLE 48

A silicone contact lens prepared in accordance with Example 46 is coated in accordance with Example 46. The treated lens is then washed in distilled water several times, and the contact angles and the water retention times are then measured.

| Silicone contact lens | Advancing angle | Receding angle | Water retention time |
|---|---|---|---|
| untreated | 120.3° | 100.8° | <3 sec. |
| treated | 59.9° | 39.4° | >20 sec. |

What is claimed is:

1. A polymer comprising a polymerization product of at least one compound of formula I and optionally of at least one other vinylic comonomer (a) that is different therefrom, wherein said formula I is

$$R^1-(COO-Alk)_m-(OCONH-R)_n-(NHCO)_p-Y-Z$$

wherein $R^1$ is an radiaclly polymerizable hydrocarbon group;

m, n and p are 0 or 1;

Alk is alkylene having up to 10 carbon atoms;

R is a diradical, having up to 20 carbon atoms, of an organic diisocyanate;

Z is a monovalent radical, minus a single hydroxy group, of a mono-, di- or tri-saccharide, of an oligosaccharide, of a cyclodextrin (CD) or of an anhydrosaccharide; and Y is —O— or —NH—, provided that m, n and p are zero when Y is —NH—.

2. A polymer according to claim 1, wherein the comonomer (a) is absent and the polymer is a homopolymer.

3. A polymer according to claim 1, wherein the proportion by weight, based on the total polymer, of a compound of formula (I) is in the range of from 100 to 0.5%, especially in the range of from 80 to 2% and preferably in the range of from 70 to 5%.

4. A polymer according to claim 1, wherein the comonomer (a) is hydrophobic and is selected from $C_1-C_{18}$alkyl and $C_3-C_{18}$cycloalkyl acrylates and methacrylates, $C_3-C_{18}$-alkyl-acrylamides and -methacrylamides, acrylonitrile, methacrylonitrile, vinyl-$C_1-C_{18}$-alkanoates, $C_2-C_{18}$alkenes, $C_2-C_{18}$haloalkenes, styrene, lower alkylstyrenes, lower alkyl vinyl ethers, $C_2-C_{10}$perfluoroalkyl acrylates and methacrylates or correspondingly partially fluorinated acrylates and methacrylates, $C_3-C_{12}$perfluoroalkyl-ethyl-thiocarbonyl-aminoethyl acrylates and methacrylates, acryloxy- and methacryloxy-alkylsiloxanes, N-vinylcarbazole, and $C_1-C_{12}$alkyl esters of maleic acid, fumaric acid, itaconic acid and mesaconic acid.

5. A polymer according to claim 1, wherein the comonomer (a) is hydrophilic and is selected from hydroxy-substituted lower alkyl acrylates and methacrylates, acrylamide, methacrylamide, lower alkyl-acrylamides and -methacrylamides, ethoxylated acrylates and methacrylates, hydroxy-substituted lower alkyl-acrylamides and -methacrylamides, hydroxy-substituted lower alkyl vinyl ethers, sodium vinylsulfonate, sodium styrene-sulfonate, 2-acrylamido-2-methylpropanesulfonic acid, N-vinylpyrrole, N-vinyl-2-pyrrolidone, 2- and 4-vinylpyridine, vinylically unsaturated carboxylic acids having a total of from 3 to 5 carbon atoms, amino-lower alkyl- (the term "amino" also including quaternary ammonium), mono-lower alkylamino-lower alkyl- and di-lower alkylamino-lower alkyl-acrylates and -methacrylates, and allyl alcohol.

6. A polymeric network consisting essentially of a polymer according to claim 1 in crosslinked form.

7. A polymeric network consisting essentially of a polymer according to claim 2 in crosslinked form.

8. A process for the preparation of a polymeric network according to claim 6, which process comprises crosslinking a polymer according to claim 1.

* * * * *